United States Patent
Mahajna et al.

(10) Patent No.: US 7,258,862 B2
(45) Date of Patent: Aug. 21, 2007

(54) MUSHROOM EXTRACTS HAVING ANTICANCER ACTIVITY

(75) Inventors: Jamal A. Mahajna, Nazareth-Illit (IL); Majed Yassin, Tamara (IL); Solomon P. Wasser, Nesher (IL)

(73) Assignees: Gavish-Galilee Bio Aplications Ltd., Glil Yam (IL); Carmel-Haifa University Economic Corp., Haifa (IL)

( * ) Notice: Subject to any disclaimer, the term of this patent is extended or adjusted under 35 U.S.C. 154(b) by 0 days.

(21) Appl. No.: 11/257,128

(22) Filed: Oct. 25, 2005

(65) Prior Publication Data

US 2006/0057157 A1  Mar. 16, 2006

Related U.S. Application Data

(62) Division of application No. 10/925,224, filed on Aug. 25, 2004, now abandoned.

(51) Int. Cl.
*A01N 65/00* (2006.01)
(52) U.S. Cl. .................. 424/195.15; 514/908
(58) Field of Classification Search ........... 424/195.15; 514/908
See application file for complete search history.

(56) References Cited

U.S. PATENT DOCUMENTS 4,051,314 A  9/1977  Ohtsuka et al.

FOREIGN PATENT DOCUMENTS

| JP | 05306233 A | 11/1993 |
|---|---|---|
| JP | 2004059558 A | 2/2004 |

OTHER PUBLICATIONS

Ottmann, O. G. et al. American Society of Hematology (2005), pp. 118-122. Acute lymphoblastic leukemia in adults: Treatment of Philadelphia chromosome-positive acute lymphoblastic leukemia.*

Giles, F. et al. Investigational New Drugs (2001), 19: 13-20. Phase I study of Irofulven (MGI 114; 6- an acylfulvene illudin analog, in patients with acute leukemia.).*

McMorris, T.C. et al. Journal of Labelled Compounds and Radiopharmaceuticals (1998), 41(4):279-285. Synthesis of [3H]-illudin S, [3H]-acylfulvene & [14C] hyroxymethylacylfulvene (MGI 114).*

Babitskaya, V.G. et al; "Exopolysaccharides of some medicinal mushrooms: Production and composition"; *International Journal of Medicinal Mushrooms*, 2000, 2(1): pp. 51-54.

Badalyan, SM et al; Chemical and pharmacological study of higher fungi. IV. Comparative investigations of the chemical composition from fruit bodies of five xylotrophic species (*Agancales* S.L); *Mikologiya I Fitopatologiya*, 1997, 31(3), pp. 61-66.

Lehmann, V.K. B. et al; Illudin S, the sole antiviral compound in mature fruiting bodies of *Omphalotus illudens*; *Journal of Natural Products*, 2003, 66(9): 1257-8.

Leitner, C. et al; "Purification and characterization of pyranose oxidase from the white rot fungus *Trametes multicolor*"; *Applied and Environmental Microbiology*, 2001, 67(8): 3636-3644.

Leon, F. et al; "Novel cytostatic Ianostanoid triterpenes from *Ganoderma australe*". *Helvetica Chimica Acta*, (2003), vol. 86, No. 9, pp. 3088-3095.

Pavia, D. L. et al; Introduction to Organic Laboratory Techniques, Third Ed., 1988, Saunders College Publishing, Chapter Technique 5: Extraction, The separatory Funnel, Drying agents, pp. 541-550.

* cited by examiner

*Primary Examiner*—Michele Flood
(74) *Attorney, Agent, or Firm*—Browdy and Neimark, PLLC

(57) ABSTRACT

The invention relates to a method for treatment of chronic myelogenous leukemia (CML), Ph+ acute lymphoblastic leukemia (ALL), prostate cancer and β-globin disorders such as sickle cell anemia and β-thalassemia, comprising administration of a mycelium extract from at least one higher Basidiomycetes medicinal mushroom selected from the group consisting of *Ganoderma adspersum, Hypsizygus ulmarium, Kuehneromyces mutabilis, Omphalotus olearius, Panus conchatus, Piptoporus betulinus, Pleurotus eryngii,* and *Trametes zonata*.

8 Claims, 4 Drawing Sheets

K562

DMSO  STI571  #540  #540
2%    1 uM    500   1000
             ug/ml

Phospho-c-Abl

Total c-Abl

MUSHROOM EXTRACTS HAVING ANTICANCER ACTIVITY

This application is a division of parent application Ser. No. 10/925,224 filed Aug. 25, 2004 now abandoned.

FIELD OF THE INVENTION

The present invention relates to extracts of medicinal mushrooms, to compositions comprising them and to methods for treatment of chronic myelogenous leukemia, Ph+ acute lymphoblastic leukemia, prostate cancer and β-globin disorders by administration of said extract or composition.

ABBREVIATIONS

ABL: Abelson leukemia virus; ALL: acute lymphoblastic leukemia; AR: androgen receptor; BCR: breakpoint cluster region; CML: chronic myelogenous leukemia; ALL: acute lymphoblastic leukemia; CV: coefficient of variance; DMSO: dimethyl sulfoxide; ELISA: enzyme-linked immunoabsorbent assay; ERK: extracellular signal-regulated kinase; HBM: higher Basidiomycetes mushrooms; HDP: host defense potentiators; HMW: high molecular weight; HSP: heat shock protein; IC50: inhibitory concentration; JNK: c-Jun N-terminal kinase; LMW: low molecular weight; MAPK: mitogen-activated protein kinase; PARP: poly(ADP-ribose) polymerase; PBS: phosphate-buffered saline; Ph: Philadelphia cromosome; Ph+: Ph positive; PSA: prostate-specific antigen.

BACKGROUND OF THE INVENTION

Higher Basidiomycetes mushrooms (HBM) represent a major and still largely untapped source of potent new pharmaceutical products. Of approximately 15,000 known species, 2,000 are safe for human consumption, and about 650 of them possess medicinal properties (Wasser et al., 2000; Hawksworth, 2001; Kirk et al., 2001; Wasser, 2002). Of about 650 mushroom species with known medicinal properties, only about 20 species are in use at the present (Chang, 2001). Most traditional knowledge about medicinal properties of HBM comes from the Far East (China, Japan, Korea, Russian Siberia). Many pharmaceutical substances with potent and unique properties have recently been extracted from mushrooms and have made their way all around the world. Unique anticancer medicines were prepared from these extracts such as polysaccharides lentinan, krestin, and schizophyllan (Mizuno, 1999).

Present studies suggest that HBM are probiotic, i.e., they help the body to strengthen itself and fight off illness by maintaining physiological homeostasis, restoring the body's balance and natural resistance to disease. The compounds they contain have been classified as Host Defense Potentiators (HDP), which can have immune system enhancement properties. That is one of the reasons why they are currently used as adjuncts to cancer treatments in many countries (Tomatis et al., 2001). In Japan, Russia, China, and the USA, several polysaccharide anticancer and immunomodulating agents have been developed from the fruiting body, mycelia, and culture medium of various medicinal mushrooms (*Lentinus edodes, Ganoderma lucidum, Schizophyllum commune, Trametes versicolor, Inonotus obliquus, Hypsizygus marmoreus,* and *Flammulina velutipes*) (Ikekawa, 2001).

Mushroom HDP include hemicellulose (AHCC), polysaccharides, polysaccharide-peptides, nucleosides, triterpenoids, complex starches, and other metabolites. It is believed that combinations of these products target the human immune system, and also aid neuron transmission, metabolism, hormonal balance, and the transport of nutrients and oxygen. Through a host-mediated (T cell) immune mechanism, they help the body regulate the development of lymphoid stem cells and other important defense responses (Mizuno, 1999).

Chronic myelogenous leukemia (CML) is a member of a group of diseases classified as myeloproliferative disorders, which account for 20% of all leukemias. CML is a clonal disorder that is usually easily recognized because the leukemia cells of more than 95% of patients suffering from CML have a distinctive cytogenetic abnormality, the Philadelphia chromosome (Ph), that results from a reciprocal translocation between the long arms of chromosomes 9 and 22. This translocation results in the transfer of the Abelson (Abl) oncogene on chromosome 9 to an area of chromosome 22 that includes the breakpoint cluster region (Bcr) gene. This results in the presentation of a leukemia-specific fusion gene (Bcr-Abl) which gives rise to an abnormal tyrosine kinase protein, p210 (Bcr-Abl), with increased activity (Clarkson et al., 1997; Cortez et al., 1997). In addition, the Ph chromosome is also found in a sizeable portion of acute lymphoblastic leukemia (ALL) patients (25-30%) and in a small number of acute myeloid leukemia (AML) cases (Drexler et al., 1999). Bcr-Abl expressing leukemic blasts are highly resistant to different classes of chemotherapeutic drugs. K562 cells, derived from patients with CML in blast crisis (Lozzio and Lozzio, 1975), which express p210 Bcr-Abl, have been shown to be highly resistant to apoptosis induced by many chemotherapeutic agents (McGahon et al., 1994). Overexpression of Bcr-Abl has been implicated in inhibiting apoptosis induced by cytokine deprivation, DNA damage, and a variety of chemotherapeutic drugs (Cortez et al., 1997). Thus, the Bcr-Abl fusion protein has been suggested to function as an antiapoptotic factor, and overexpression of the Bcr-Abl protein in K562 cells may, in part, account for the resistance of these cells to apoptosis, thereby leading to the accumulation of leukemic blasts in patients with chronic myeloid leukemia (Urbano et al., 1998).

Gleevec (imatinib mesylate, also known as STI-571), is being used as oral treatment for patients with CML. It is a protein-tyrosine kinase inhibitor that inhibits the Bcr-Abl tyrosine kinase.

Apoptosis, programmed cell death, is a genetically controlled ablation of cells during development. It is characterized by chromatin condensation, nuclear fragmentation, cell membrane blebbing, apoptotic body formation, and mitochondrial changes, including enhanced membrane permeability, fall of mitochondrial membrane potential ($\Delta\psi m$), and release of cytochrome c into the cytosol. Induction of apoptosis is the principal mechanism by which the majority of chemotherapeutic agents exert their function. Consequently, failure to undergo apoptosis is the likely mechanism mediating drug resistance in tumors.

Antitumor and anticancer properties have been studied in mushrooms. The three mushrooms which have the broadest range of action are Shiitake (*Lentinus edodes*), Reishi (*Ganoderma lucidum*) and Maitake (*Grifola frondosa*). Another popular mushroom is *Coriolus versicolor*, also known as *Trametes versicolor*.

Among the main active substances found in medicinal mushrooms are:

(i) lentinan, a highly purified polysaccharide fraction extracted from Shiitake mushrooms, is an approved drug in Japan. It is generally administered by injection and has been used as an agent to prolong survival of patients in conventional cancer therapy, for example, in bowel cancer, liver cancer, stomach cancer, ovarian cancer and lung cancer; it also stimulates the production of T-lymphocytes and natural killer cells and can potentiate the effect of AZT in the antiviral treatment of AIDS;

(ii) a substance known as activated hexose-containing compound (AHCC) or 1,3-beta glucan is an active fraction found in shiitake mushrooms which has shown anti-cancer properties in some human, animal and lab studies in Japan;

(iii) polysaccharide-peptide or PSP, a proteoglycan from *Trametes versicolor*, also known as *Coriolus versicolor*, has been widely used in China as anticancer and immunomodulatory agent in the treatment of patients with cancer of the stomach, esophagus, lung, ovary and cervix;

(iv) the immunostimulating polysaccharide krestin, polysaccharide-K or PSK is a popular Japanese extract made from *Trametes versicolor*. PSK has been shown in several studies to help cancer patients undergoing chemotherapy, and significantly extended survival at five years or beyond in cancers of the breast, liver, prostate, stomach, colon-rectum, esophagus, nasopharynx, and lung (non-small cell types). PSK acts directly against tumor cells as well as indirectly in the host to boost cellular immunity by increasing white cell activity and increasing natural killer cell function. The list of cancers for which it is known to be useful in animals includes adenosarcoma, fibrosarcoma, mastocytoma, plasmacytoma, melanoma, sarcoma, carcinoma, mammary cancer, colon cancer, and lung cancer; and (v) a dietary supplement prepared from extracts of *Trametes versicolor* is in use for general health purposes. Ethanol extracts (70%) of *Trametes versicolor* dietary supplement reduced LNCaP cell growth and down-regulated the levels of secreted prostate specific antigen (PSA), raising the possibility of chemopreventive potential for hormone-refractory prostate cancer (Hsieh and Wu, 2001).

We have not found in the literature any publication disclosing the activity of mushroom extracts on CML cells.

Although most bioactive substances isolated from mushrooms are high-molecular-weight (HMW) polysaccharides, our interest is in low-molecular-weight (LMW) compounds capable of exhibiting antitumor activity. We have thus focused on the search for novel compounds that induce apoptosis in CML cells and might be useful in the therapy of patients with CML.

SUMMARY OF THE INVENTION

It has now been found, in accordance with the present invention, that mycelium extracts of some higher Basidiomycetes mushrooms selectively inhibit the growth, promote apoptosis, and induce erythroid differentiation of K562 cells, a human CML cell line, and also inhibit the growth of LNCaP cells, a human hormone-responsive prostate cancer cell line.

The present invention thus relates, in one aspect, to a composition comprising a mycelium extract from at least one higher Basidiomycetes medicinal mushroom selected from the group consisting of *Ganoderma adspersum*, *Hypsizygus ulmarium*, *Kuehneromyces mutabilis*, *Omphalotus olearius*, *Panus conchatus*, *Piptoporus betulinus*, *Pleurotus eryngii*, and *Trametes zonata*, said composition having selective antiproliferative activity, or selective apoptosis-inducing activity on the human chronic myelogenous leukemia K562 cells and on the human prostate cancer LNCaP cells.

The compositions may be in the form of pharmaceutical compositions or they may be comprised within a food or beverage.

Further provided are methods for the treatment of a patient suffering from CML, ALL, prostate cancer or a β-globin disorder consisting of sickle cell anemia and β-thalassemia, which comprises administration of a composition of the invention to said patient in need.

DETAILED DESCRIPTION OF THE INVENTION

Figure 1:
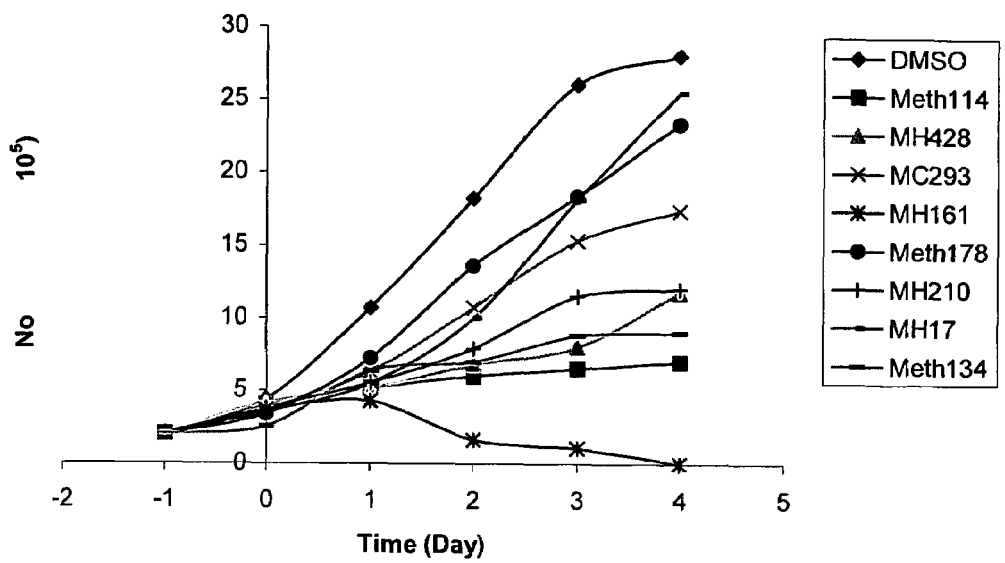
FIG. 1 shows the effect of mycelium crude extracts on the viability of K562 cells. K562 cells were plated in 6-well plates at $1\times10^5$ cells/ml (Day −1). Twenty-four hours later (Day 0), 500 µg/ml of mycelium crude extracts Meth114, MH428, MC293, MH161, Meth178, MH210, MH17, and Meth134 (see Tables 1 and 3 for mushroom species) were added and cell numbers were monitored for 4 days by trypan blue exclusion assay as described in Materials and Methods. Experiments were carried out in duplicate. Changes in duplicate samples were minimal with % CV below 10% in all experiments. This experiment was repeated twice with similar outcomes.

The present invention provides novel extracts of higher Basidiomycetes medicinal mushrooms selected from the group consisting of *Ganoderma adspersum*, *Hypsizygus ulmarium*, *Kuehneromyces mutabilis*, *Omphalotus olearius*, *Panus conchatus*, *Piptoporus betulinus*, *Pleurotus eryngii*, and *Trametes zonata*, said extracts being obtained from dry mycelium of the mushrooms by solvent extraction. Preferred mushrooms are *Omphalotus olearius*, more preferably the strain *Omphalotus olearius* (DC.:Fr.)Fr., *Piptoporus betulinus*, more preferably the strain *Piptoporus betulinus* (Bull.:

Fr.) P. Karst., and *Trametes zonata*, more preferably the strain *Trametes zonata* (Nees.:Fr.) Pilat.

The extraction is performed with an extraction solvent comprising one or more organic solvents, and optionally comprising water. Examples of organic solvents that can be used according to the invention are, without being limited to, methanol, ethanol, acetonitrile, ethyl acetate, chloroform, hexane, cyclohexane, isooctane and dichloromethane.

In one embodiment, the extraction solvent is a sole organic solvent used alone, e.g. dichloromethane (DCM), methanol or ethanol, or together with water, preferably ethanol, more preferably 70% ethanol. In another embodiment, the solvent is a mixture of two organic solvents, optionally with water, such as methanol and ethyl acetate, preferably 10-60% methanol and 20-40% ethyl acetate, more preferably, 11% methanol and 22% ethyl acetate or 50% methanol and 33% ethyl acetate, or methanol and chloroform, preferably 50% methanol and 33% chloroform.

The mushrooms are grown initially in agar plates at 27° C. and are then transferred to liquid media and grown in a suitable medium in submerged conditions for about 2-3 weeks. Dry mycelium is extracted with the solvents of choice and tested for biological activity.

As used herein in the specification, the terms and phrases set out below have the meanings which follow:

For the extraction solvents, "Eth" means 70% ethanol, "E" means a mixture of 33% ethyl acetate and 50% methanol, "H" means a mixture of 22% ethyl acetate and 11% methanol, "C" means a mixture of 33% chloroform and 50% methanol (the remainder in these cases is water), and "DCM" means 100% dichloromethane. The letters C, E, H Eth, and DCM also appear in the designation of the extracts as defined below and in the examples.

"MH161" means the crude mycelium extract of *Kuehneromyces mutabilis*, strain 18 in Table 1 hereinafter, in solvent H.

"MH210" means the crude mycelium extract of *Pleurotus eryngii*, strain 13 in Table 1 hereinafter, in solvent H.

"Meth178" means the crude mycelium extract of *Omphalotus olearius*, strain 12 in Table 1 hereinafter, in solvent Eth.

"MH17" means the crude mycelium extract of *Piptoporus betulinus*, strain 11 in Table 1 hereinafter, in solvent H.

"Meth134" means the crude mycelium extract of *Ganoderma adspersum*, strain 8 in Table 1 hereinafter, in solvent Eth.

"Meth114" means the crude mycelium extract of *Panus conchatus*, strain 7 in Table 1 hereinafter, in solvent Eth., "MC293" means the crude mycelium extract of *Hypsizygus ulmarium*, strain 4 in Table 1 hereinafter, in solvent C.

"MH428" means the crude mycelium extract of *Trametes zonata*, strain 1 in Table 1 hereinafter, in solvent H.

"Meth162" means the crude mycelium extract of *Kuehneromyces mutabilis*, strain 18 in Table 1 hereinafter, in solvent Eth.

"Meth215" means the crude mycelium extract of *Pleurotus eryngii*, strain 13 in Table 1 hereinafter, in solvent Eth.

"Meth 194" means the crude mycelium extract of *Pholiota Aurivella*, strain 31 in Table 1 hereinafter, in solvent Eth.

"Meth327" means the crude mycelium extract of *Trametes zonata*, strain 1 in Table 1 hereinafter, in solvent Eth.

"DCM540" means the crude mycelium extract of *Trametes zonata*, strain 1 in Table 1 hereinafter, in solvent DCM.

"K562 cells" means the human chronic myelogenous leukemia cell line.

Once obtained, the extracts are tested for antiproliferative activity on the K562 cells. Extracts that inhibit the growth of K562 cells, but do not inhibit the growth of other tumor or normal cells, are specific to the K562 cells and are suitable candidates for treatment of CML. The extracts may be further tested to see whether they promote apoptosis in K562 cells, in which case they will be more preferred candidates for treatment of CML patients.

The extracts selective for K562 cells are also tested to see whether they induce erythroid differentiation in K562 cells. Extracts that induce erythroid differentiation are suitable candidates for treatment of a β-globin disorder such as sickle cell anemia and β-thalassemia, The extracts are also tested for antiproliferative activity on human prostate cancer LNCaP cells. Extracts that inhibit the growth of LNCaP cells, but do not inhibit the growth of other tumor or normal cells, are specific to the LNCaP cells and are suitable candidates for treatment of prostate cancer. The extracts may be further tested to see whether they promote apoptosis in LNCaP cells, in which case they will be more preferred candidates for treatment of prostate cancer patients.

Thus, according to the present invention, 42 species of HBM were cultivated as pure cultures in submerged conditions, and dry mycelium were used to prepare 168 different crude extracts. The crude extracts were used to evaluate antiproliferative activity against a number of cancer cell lines, including K562, Jurkat (human T lymphoblast cells), HT29 (human colon adenocarcinoma cells), MH3924A (rat Morris hepatoma), and ABAE (adult bovine aortic endothelial cells) using XTT proliferation assay.

Forty-four different crude extracts were selected with antiproliferative effect against K562 cells and eight mycelium extracts were K562-selective compared with MH3924A, HT29, ABAE, and Jurkat cells. Growth inhibition against K562 ranged from 51% to 78% compared with solvent-treated samples. Most crude extracts exhibited a complete or partial cytostatic effect against K562 cells.

The antiproliferative effect observed by the selected crude extracts was attributed to the induction of apoptosis pathway as determined by Apostain ELISA assay and by monitoring PARP cleavage. Interestingly, crude extract MH428 was the most active extract in inducing apoptosis of K562 cells.

In addition, expression levels of $p210^{Bcr-Abl}$ were affected by the presence of the selected crude extracts. Our data revealed a significant inhibition of $p210^{Bcr-Abl}$ expression by MH428 extract, a moderate effect by MH17, and minor changes by the other extracts.

Furthermore, mycelium crude extracts were active in inducing erythroid differentiation in K562 cells. Crude extracts Meth178, MH17, and MH428 show significant ability to induce hemoglobin production in K562 cells as indicative of erythroid differentiation.

Data presented in accordance with the present invention illustrate the potential of the mycelium extracts, particularly the MH428 extract, in CML therapy. This extract was prepared from *Trametes zonata* and was also active against LNCaP cells, indicating that *Trametes zonata* extract is active in inhibiting hormone-refractory prostate cancer cells.

The mycelium extracts obtained as described above are concentrated and purified for human use. Concentration can be carried out by conventional techniques such as thermal, decompressing thermal, activated carbon or ion exchange resin methods. The concentrated extract is then purified to yield a purified extract of one or more purified compositions using standard techniques such as column chromatography, fractional distillation, preparative TLC (thin layer chromatography), preparative HPLC (high performance liquid chromatography), CPC (centrifugal partition chromatography)

or other techniques known to those skilled in the art. After concentration and purification, the product is dried by any conventional technique such as air-dry, hot-blast drying, spray dry, and freeze-dry methods.

The invention also provides a composition comprising a mycelium extract of the invention. The composition may be a pharmaceutical composition, in which case the extract is in admixture with one or more pharmaceutically acceptable carriers. The composition may also be in the form of food or beverage.

For formulation of the compositions of the invention, powders of the extract may be used in that form directly as a loose powder or encapsulated powder, or may be formulated into capsules, caplets, tablets and similar dosage forms. Further, powders may be formulated within liquid pervious membranes such as filters, meshes and the like, such as a tea bag-type infuser, for generating liquids containing the dissolved extract. The powder form of the extract may also be incorporated into liquids, formulated as solutions, dispersions or suspensions by dissolving the extract, for example as a drink, tincture, or drop. The extract may be administered alone, or with a carrier.

The extract can be prepared alone or as an active ingredient in pharmaceutical compositions including non-toxic, pharmaceutically acceptable carriers, diluents and excipients, as are well known in the art (see, for example Merck Index, Merck & Co., Rahway, N.J.; and Gilman et al., (eds) (1996) Goodman and Gilman's: The Pharmacological Bases of Therapeutics, 8.sup. th Ed., Pergamon Press). For standard dosages of conventional pharmacological agents, see, e.g., Physicians Desk Reference (1997 Edition); and U.S. Pharmacopeia National Formulary (1995) United States Pharmacopeial Convention Inc., Rockville, Md. Compositions may also include flavors, colorings, coatings, etc. All agents must be non-toxic and physiologically acceptable for the intended purpose, and must not substantially interfere with the activity of the extract so as to deleteriously affect the desired biological activity thereof. Ingredients are thus only included in therapeutically acceptable amounts The dosage of the extract to be administered depends upon many factors that are well known to those skilled in the art, for example, the particular form of the extract; the stage of the disease; the age, weight and clinical condition of the patient; any concurrent therapeutic treatments; and the experience and judgment of the clinician or practitioner administering the therapy. The extract may be administered orally, intraperitoneally, or intravenously at a dosage range and frequency (e.g., at least once daily) such that the level of active extract is maintained in the body. The dosage range varies with the route of administration, and the form and potency of the extract; for example, one dose of the extract in a capsule taken orally may contain for example 100-2000 mg of the extract, preferably 200-1500 mg, more preferably 250-1000 mg, still more preferably 500-800 mg. The extract is preferably administered in spaced dosages throughout the day to maintain the level of active extract in the body.

The present invention further provides food or beverage containing a composition of the invention. Thus, for example, the extract may be added to fruit juice, vegetable juice, all kinds of tea and nutrient drinks possibly containing nutraceuticals of choice such as vitamins, minerals, antioxidants and the like.

The invention further provides a method of treating a Philadelphia chromosome-positive ($Ph^+$) leukemia patient such as CML and ALL $Ph^+$ leukemia patients, comprising administering to a patient in need a therapeutically effective amount of a composition of the invention, preferably a composition comprising a mycelium extract of *Piptoporus betulinus* or *Trametes zonata*.

Further provided by the invention is a method of treating sickle cell anemia comprising administering to a patient in need a therapeutically effective amount of a composition of the invention, preferably a composition comprising a mycelium extract of of *Omphalotus olearius, Piptoporus betulinus*, or *Trametes zonata*.

The invention still further relates to a method of treating β-thalassemia comprising administering to a patient in need a therapeutically effective amount of a composition of of the invention, preferably a composition comprising a mycelium extract of of *Omphalotus olearius, Piptoporus betulinus*, or *Trametes zonata*.

The invention yet further provides a method of treating prostate cancer comprising administering to a patient in need a therapeutically effective amount of a composition of the invention, preferably a composition comprising a mycelium extract of *Trametes zonata*.

The invention will now be illustrated by the following non-limiting Examples.

EXAMPLES

Materials and Methods (i) Mushroom Species, Cultivation and Extraction

The strains used in the present invention are from a culture collection of HBM (acronym HAI) of the Institute of Evolution, University of Haifa, Israel (Wasser et al., 2002), that contains presently over 1000 strains of edible and medicinal mushrooms. About 200 species were collected in different ecological regions of Israel, and new strains have been permanently introduced into the collection. The collection also contains many diverse strains of well-known medicinal mushrooms from North America, Europe, and other parts of the world. Table 1 hereinafter shows a list of mushroom species used to prepare the mycelium crude extracts tested herein. Mushrooms were grown initially in agar plates at 27° C., and then transferred to liquid media to generate a starter culture. Large-scale growth was carried out in 500 ml liquid medium in 2-liter Erlenmeyer for 2-3 weeks at 27° C. with shaking at 180 rpm.

Medicinal mushrooms were grown in submerged condition, and mycelium was dried and used to prepare crude extracts using various mixtures of aqueous organic solvents, including Eth (70% ethanol), E (33% ethyl acetate, 50% methanol), H (22% ethyl acetate, 11% methanol), and C (33% chloroform, 50% methanol). Obtained yield of crude extract with the various mixtures of organic solvents is shown in Table 1 in mg/gram of dried mycelium used. ND indicates 'not determined'.

(ii) Mushroom Growth Medium

Mushrooms were grown in liquid or solid media containing 2% glucose, 0.1% bacteriological peptone, 0.1% yeast extract, 0.1% $KH_2PO_4$, 0.1% $MgSO_4$, and 1.7% of a Bacto-Agar in agar plates. The media were also supplemented with 10 ml per 1 liter of trace solution (18 mM $FeSO_4$, 3.7 mM $MnSO_4$, 1.5 mM $ZnSO_4$, 0.8 mM $CuSO_4$).

(iii) Preparation of Mycelium Crude Extracts

Dry mycelium was extracted with the four solvents Eth, C, E and H (see (i) above) (1 gram of material used for each condition).

(iv) Cell Lines and Cell Cultures

Human K562, Jurkat, and HT-29 cell lines were grown in RPMI 1640 medium with L-glutamine supplemented with 10% fetal bovine serum. Bovine aortic arch-derived endothelial cell (ABAE) and rat Morris hepatoma MH3924A cells were grown in DMEM and supplemented with 10% fetal bovine serum. Human LNCaP prostate cells were maintained in RPMI 1640 medium supplemented with 10% fetal calf serum. Penicillin at 100 U/ml and streptomycin at 100 µg/ml were added to the culture media. All cell lines were grown at 37° C. in a humidified atmosphere with 5% $CO_2$. Adherent cell lines were transferred with 0.025% trypsin and 0.02% EDTA.

(v) Cell Viability

To determine cell growth and viability, K562 cells ($2 \times 10^5$ cells/ml) in triplicate were incubated in 2 ml of RPMI 1640-10% fetal calf serum (FCS) containing mycelium crude extracts or DMSO. The volume of the DMSO was kept at 0.6% of the medium volume. At the indicated times, cell viability was determined by the trypan blue exclusion assay (Freshney, 1987). At least 200 cells were examined in each sample. Data were expressed as % of inhibition relative to solvent-treated samples.

(vi) Erythroid Differentiation

Erythroid differentiation was determined by monitoring levels of hemoglobin production in treated cells. K562 cells were plated in 6-well plates at $2 \times 10^5$ cells/ml, followed by treatment with various concentrations of mycelium extracts for 5 days. Cells were washed with phosphate-buffered saline (PBS) and cell pellet was re-suspended in 100 µL lysis buffer (100 mM potassium phosphate pH 7.8, 0.2% Triton X-100) and incubated for 10 min at room temperature. Intracellular hemoglobin levels were determined by means of the plasma hemoglobin kit from Sigma (USA) according to the manufacturer's instructions. Levels of hemoglobin were normalized to protein concentration found in each sample. Protein concentration was determined by DC Protein Assay Kit (Bio-Rad, USA) according to manufacturer's instructions. Relative hemoglobin levels were calculated in relation to solvent-treated sample, which was designated 1.0.

(vii) XTT Cell Proliferation Assay

The XTT assay for fungal viability is based on the MTT assay (Mosmann, 1983) used to monitor cell proliferation growing in suspension. In brief, K562 cells were seeded in 96-well plates at $1.5 \times 10^4$ cells/well; 24 hours later cells were treated with mycelium crude extracts at 1 mg/ml and 250 µg/ml for an additional 24 hours. 50 µL of XTT solution at 1.5 µg/ml were added to each well and were incubated for three hours at 37° C. The optical density was measured by multiwell plate spectrophotometer at 405 nanometers.

(viii) PARP Cleavage

To analyze poly(ADP-ribose) polymerase (PARP) cleavage (Dou et al., 1999), cells ($2 \times 10^5$ cells/ml) were treated with mycelium crude extracts or DMSO for the indicated time. Cells were collected, washed once with cold PBS, and lysed in buffer [10 mM Tris-HCl (pH 7.4), 100 mM NaCl, 1 mM EDTA, 1 mM EGTA, 1 mM NaF, 20 mM $Na_4P_2O_7$, 2 mM $Na_3VO_4$, 1% Triton X-100, 10% glycerol, 0.1% SDS, 0.5% deoxycholate, 1 mM phenylmethylsulfonyl fluoride] for 30 min at 4° C. Cell lysate supernatants (40 µg protein/each) were resolved on 8% SDS-PAGE, transferred to nitrocellulose membranes, and analyzed by immune-blotting with an anti-PARP antibody (Santa Cruz Co., USA).

(ix) Apostain ELISA Assay

K562 cells ($1 \times 10^5$ cells/ml) were treated with mycelium crude extracts or DMSO for 48 hours. Samples were collected, washed with PBS, resuspended in 100 µl of 80% methanol, and kept at −20° C. for 2-3 days. Between 2500 and 5000 cells were used for Apostain ELISA assay according to manufacturer's instructions (Alexis Biochemical, USA).

(x) Bcr-Abl Phosphorylation Assay

K562, BaF3/Bcr-Abl wild-type (WT), BaF3/Bcr-Abl T315I and BaF3/Bcr-Abl E255K cell lines were seeded 4 mls/well in 6-well plates at $5-6 \times 10^5$ cells/ml. Control cells were treated with 2% DMSO. Gleevec-treated cells were treated with 1 µM Gleevec and dichloromethane (DCM) extract of T. zonata (# 540) at two concentrations: (A) at 500 µg/ml and (B) at 1000 µg/ml, that were added after 24 hours. Cells were treated for 60 min, then collected and centrifuged at 5000 rpm for 5 min. Cell pellets were lysed in lysis buffer (10 mM Tris, pH 7.4; 100 mM NaCl; 1 mM EDTA; 1 mM EGTA; 1 mM NaF; 20 mM $Na_4P_2O_7$; 2 mM $Na_3VO_4$; 1% Triton-X100; 10% glycerol; 0.1% SDS; 0.5% deoxycholate; 1 mM PMSF; 10 µl protease inhibitor cocktail and phosphatase inhibitor cocktail were added to every 1 ml lysate}. After that, 40 µg protein from each sample were separated on 8% SDS-PAGE, then Western blot was performed according to the manufacturer's instructions using phospho-c-Abl (Tyr245) Antibody (Cell Signaling Technology Co.) and c-Abl monoclonal antibody (Santa Cruz Biotechnology).

Example 1

Identification of Mycelium Crude Extracts that Inhibit Proliferation of K562 Cells A large number of medicinal mushrooms (42) shown in Table 1 were cultivated in submerged conditions, and extracted with various extraction solvents (4), as described in Materials and Methods, resulting in the preparation of 168 crude mycelium extracts. The mycelium was dried and used to prepare crude extracts using various mixtures of organic solvents including Eth (70% ethanol), E (33% ethyl acetate, 50% methanol), H (22% ethyl acetate, 11% methanol), and C (33% chloroform, 50% methanol). The obtained yield of crude extract with the various organic solvents is shown in Table 1 in mg of crude extract/gram of dried mycelium. ND indicates not determined.

Crude extracts were screened for their ability to inhibit the growth of K562, a human chronic myelogenous leukemia blast cell. Growth inhibition was evaluated by XTT assay as described in Materials and Methods. Cleavage of the tetrazolium salt XTT, sodium 3'-[1-[(phenylamino)-carbonyl]-3,4-tetrazolium]-bis(4-methoxy-6-nitro)benzene-sulfonic acid hydrate, by dehydrogenase enzymes of metabolically active cells yields a highly colored formazan product, which is water soluble. This feature obviates the need for formazan crystal solubilization prior to absorbance measurements, as required with the use of other tetrazolium salts such as MTT, and offers a simple method for evaluating proliferation of cells growing in suspension such as K562 cells (Roehm et al., 1991).

TABLE 1

List of mushroom species tested and yield of various crude extracts prepared from mycelium of submerged cultures

| | | | mg crude extract/g dry mycelium | | | |
|---|---|---|---|---|---|---|
| No. | Species, authors | HAI strain number | C | E | H | Eth |
| 1 | *Trametes (T.) zonata* (Nees.: Fr.) Pilat | 540 | 183 | 64 | 16 | 110 |
| 2 | *T. multicolor* (Schaeff.) Julich | 428 | 100 | 90 | 70 | 50 |
| 3 | *T. hirsutus* (Wulf.: Fr.) Pilat | 598 | 376 | 340 | 462 | 418 |
| 4 | *Hypsizygus (H.) ulmarium* (Bull.: Fr.) Redhead | 812 | 55 | 88 | 107 | 96 |
| 5 | *H. decastes* (Fr.) Sing | 510 | 117 | 107 | 93 | 107 |
| 6 | *H. marmoreus* (Peck) Bigel. | 609 | 144 | 91 | 82 | 96 |
| 7 | *Panus conchatus* (Bull.: Fr.) Fr. | 396 | 100 | 100 | 100 | 80 |
| 8 | *Ganoderma adspersum* (S. Schulz.) Donk | 349 | 245 | 100 | 230 | 180 |
| 9 | *G. applanatus* (Pers.: Wallr.) Pat. | 604 | 210 | 160 | 200 | 215 |
| 10 | *G. resinaceum* Boud. | 142 | 220 | 170 | 210 | 220 |
| 11 | *Piptoporus betulinus* (Bull.: Fr.) P. Karst. | 241 | 240 | ND | 200 | ND |
| 12 | *Omphalotus olearius* (DC.: Fr.) Fr. | 173 | 110 | 100 | 115 | 140 |
| 13 | *Pleurotus (P.) eryngii* (DC.: Fr.) Quel. | 202 | 156 | 131 | 169 | 100 |
| 14 | *P. ostreatus* (Jacq.: Fr.) Kumm. | 592 | 200 | 80 | 70 | 100 |
| 15 | *P. salignus* (Fr.) Kumm. | 571 | 75 | 44 | 75 | 69 |
| 16 | *P. cystidiosus* O. K. Miller | 140 | 169 | 146 | 133 | 108 |
| 17 | *P. pulmonarius* (Fr.) Quel. | 573 | 169 | 108 | 75 | 116 |
| 18 | *Kuehneromyces mutabilis* (Schaeff.: Fr.) Sing et A. H. Sm. | 114 | 100 | 70 | 100 | 120 |
| 19 | *Rigidoporus ulmarius* (Sow.: Fr.) Imazeki | 439 | 60 | 60 | 70 | 60 |
| 20 | *Spongipellis litshaueri* Lohw | 444 | 100 | 100 | 60 | 100 |
| 21 | *Panellus (P.) stipticus* (Bull.: Fr.) P. Karst. | 520 | 100 | 90 | 90 | 70 |
| 22 | *P. serotinus* (Pers.: Fr.) Kuhn | 498 | 169 | 119 | 125 | 156 |
| 23 | *Gloeophyllum odoratum* (Wulf.) Imazeki | 337 | 100 | 70 | 90 | 90 |
| 24 | *Schizophyllum commune* Fr.: Fr. | 632 | 90 | 60 | 80 | 50 |
| 25 | *Oudemansiella radicata* (Relh.: Fr.) Sing | 773 | 170 | 130 | 180 | 150 |
| 26 | *O. mucida* (Schrad.: Fr.) Hoehn. | 181 | 170 | 100 | 140 | 130 |
| 27 | *Leucoagaricus (L.) carneifolius* (Gill.) S. Wasser | 344 | 110 | 65 | 100 | 98 |
| 28 | *L. leucothitus* (Vitt.) S. Wasser | 282 | 185 | 160 | 155 | 160 |
| 29 | *Marasmius scorodonius* (Fr.) Fr. | 784 | 290 | 160 | 70 | 150 |
| 30 | *Polyporus squamous* Huds.: Fr. | 242 | 180 | 75 | 140 | 80 |
| 31 | *Pholiota aurivella* (Batsch.: Fr.) Kumm. | 236 | 125 | 80 | 65 | 88 |
| 32 | *Grifola frondosa* (Dicks.: Fr.) S. F. Gray | 270 | 173 | 152 | 193 | 133 |
| 33 | *Fomes fomentarius* (L.: Fr.) Fr. | 383 | 163 | 138 | 63 | 125 |
| 34 | *Lentinus edodes* (Berk.) Sing | 313 | 187 | 193 | 200 | 207 |
| 35 | *Phellinus ignarius* (L.: Fr.) Quel. | 785 | 131 | 113 | 138 | 103 |
| 36 | *Merulius tremellosus* Fr. | 267 | 286 | 120 | 320 | ND |
| 37 | *Irpex lacteus* (Fr.: Fr.) Fr. | 532 | 178 | 168 | 176 | 152 |
| 38 | *Inonotus levis* P. Karst. | 796 | 174 | 144 | 115 | 118 |
| 39 | *Flammulina velutipes* (Curt.: Fr.) Sing | 105 | 153 | 64 | 125 | 58 |
| 40 | *Oxyporus obducens* (Fr.) Donk | 824 | 97 | 95 | 109 | 108 |
| 41 | *Agaricus langei* (Moell.) Moell. | 295 | 88 | 102 | 46 | 86 |
| 42 | *Funalia trogii* (Berk. upud. Trog.) Bond. et Sing | 352 | 200 | 130 | 150 | 60 |

Antiproliferative activity of crude mycelium extracts was evaluated against K562 cells. K562 cells were plated in 96-well plates at $1.5 \times 10^4$ cells/well and 24 hours later were treated with mycelium crude extracts at 250 µg/ml and 1 mg/ml (with addition of 10 µl of stock solution to each well containing 100 µl of K562 cells). Twenty-four hours later, XTT assay was performed as described in Materials and Methods.

The obtained results are summarized in Table 2. A total of 44 crude extracts from the 168 screened extracts were active in inhibiting the growth of K562 cells by more than 50%. The 44 crude mycelium extracts represent about 26% of the screened extracts. The number of active extracts among the various extraction methods varied significantly. With solvent mixtures H (22% ethyl acetate, 11% methanol), E (33% ethyl acetate, 50% methanol), C (33% chloroform, 50% methanol), and Eth (70% ethanol), the number of K562 active extracts were 5, 13, 12, and 14, respectively (Table 2).

TABLE 2

Distribution of K562 active mycelium crude extracts among the different organic mixtures

| | Number | | | | | % | | | | |
|---|---|---|---|---|---|---|---|---|---|---|
| Extracts | Total | H | E | C | Eth | Total | H | E | C | Eth |
| Screened | 168 | 41 | 43 | 42 | 42 | 100 | 24.4 | 25.6 | 25 | 25 |
| Active (>50%) | 44 | 5 | 13 | 12 | 14 | 26 | 11.4 | 29.5 | 27.3 | 31.8 |
| Selective | 8 | 4 | 0 | 1 | 3 | 18.2 | 50 | 0 | 12.5 | 37.5 |

Example 2

Identification of Mycelium Crude Extracts that Selectively Inhibit Proliferation of K562 Cells The K562 active crude extracts of Example 1 were subjected to selectivity evaluation by monitoring growth inhibition of the selected extracts against other cell lines, including Jurkat (human T lymphoblasts), HT29 (human colon adenocarcinoma cells), MH3924A (rat Morris hepatoma), and ABAE (adult bovine aortic endothelial cells).

Cells were plated in 96-well plates at $1.5 \times 10^4$ cells/well. Twenty-four hours later mycelium crude extracts were added for an additional 24 hours followed by XTT determination according to manufacturer's instructions (Biological Industries, Isreal). Percentage of growth inhibition was calculated in relation to solvent-treated samples. Experiments were carried out in duplicate. The results are shown in Table 3. Changes in % coefficient of variance (CV) among duplicate samples were minimal. For example, % CV in growth inhibition of K562 using duplicate samples treated with mycelium crude extracts MH161, MH210, Meth178, MH17, Meth134, Meth114, MC293, MH428 were 0.4, 28, 6.4, 1.1, 4.3, 1.9, 17.9, 4.1, respectively. This experiment was repeated twice with similar outcomes.

Mycelium crude extracts that inhibited K562 by more than 50% and showed minimal growth inhibition (less than 30% inhibition) against other cell lines were designated as selective K562 inhibitors. Table 3 shows a list of selective mycelium crude extracts (with their designations and identification of the mushroom strain in the first two columns) with percentage of growth inhibition applied to a variety of cell lines. Growth inhibition was calculated compared with solvent-treated samples.

It is important to note that XTT assay does not distinguish between cytostatic and cytotoxic effects in continuously proliferating cultures. Therefore, the effect of the selected mycelium crude extracts on the viability of K562 cells was evaluated. Although cell viability can be reflected by a variety of different parameters, integrity of the outer cell membrane is often used. The vital dye trypan blue, which is usually excluded from viable cells, was used to assess whether mycelium crude extracts function as a cytotoxic or a cytostatic compound against K562 cells. Cells were treated with 500 μg/ml of the appropriate crude extracts shown in Table 3 and viable cells were monitored for several days.

K562 cells were plated in 6-well plates at $1 \times 10^5$ cells/ml (day −1). Twenty-four hours later (day 0), 500 μg/ml of mycelium crude extracts Meth114, MH428, MC293, MH161, Meth178, MH210, MH17, and Meth134 (see Table 3 for mushroom species) were added and cell numbers were monitored for 4 days by trypan blue exclusion assay as described in Materials and Methods.

The results shown in FIG. 1 illustrate that most mycelium crude extracts exhibit a complete (MH210, Meth134, Meth114, MH326) or partial (Meth178, MH17, MC293) cytostatic effect. In contrast, crude extract MH161 exhibited cytotoxic effect at the concentration used.

Example 4

Involvement of the Apoptosis Pathway in Mediating the Growth Inhibition of K562 Cells by Mycelium Crude Extracts

TABLE 3

Effect of K562-selective mycelium crude extracts on the growth of K562, MH3924A, ABAE, HT-29 and Jurkat cell lines

| | | | | % of Growth Inhibition | | | | |
|---|---|---|---|---|---|---|---|---|
| Ext | Mushroom | Strain | Solvent | K562 | MH3924A | ABAE | HT-29 | Jurkat |
| MH 161 | *Kuehneromyces mutabilis* | 114 | H | 61.3 | 16.6 | −30.1 | −19.5 | 16.2 |
| MH 210 | *Pleurotus eryngii* | 202 | H | 53.8 | 3.4 | −34.0 | −27.2 | 8.8 |
| Meth 178 | *Omphalotus olearius* | 173 | Eth | 56.9 | −14.5 | −56.2 | −11.3 | −36.4 |
| MH 17 | *Piptoporus betulinus* | 241 | H | 68.8 | 15.2 | 28.2 | −7.6 | −2.9 |
| Meth 134 | *Ganoderma adspersum* | 349 | Eth | 59.2 | −15.5 | −44.7 | 23.1 | −18.4 |
| Meth 114 | *Panus conchatus* | 396 | Eth | 56.0 | 11.5 | 27.8 | 4.3 | 2.4 |
| MC 293 | *Hypsizygus ulmarium* | 812 | C | 56.7 | 14.4 | −28.9 | −7.6 | 7.3 |
| MH 428 | *Trametes zonata* | 540 | H | 69.0 | −11.4 | −5.1 | 1.9 | 30.1 |

Table 3 shows that a total of 8 mycelium crude extracts exhibited selective activity against K562 cells. The 8 positive crude extracts were distributed among the various extraction methods as follows: 4, 0, 1, and 3 using organic mixture H, E, C, and Eth, respectively. It is interesting that most of the selective extracts were extracted by means of the H and Eth organic solvents.

Example 3

Effect of the Mycelium Crude Extracts on the Viability of K562 Cells

Apoptosis, programmed cell death, is a genetically controlled ablation of cells during development. Furthermore, induction of apoptosis is the principal mechanism by which the majority of chemotherapeutic agents exercise their function. Accordingly, we evaluated whether our mycelium crude extracts affected the apoptosis pathway in K562 cells. Our data show that 8 mycelium crude extracts exhibited selective antiproliferative effect against K562 cells as determined by XTT assay (Table 3) and trypan blue exclusion assay (FIG. 1).

To evaluate whether the antiproliferative effect of mycelium crude extracts is mediated by induction of the apoptosis process, we monitored changes in chromatin condensation as a marker of apoptosis (Allera et al., 1997). A recent report illustrated that formamide, a gentle denaturing agent, denatured DNA in apoptotic cells, but not in necrotic cells (Frankfurt and Krishan, 2001a, b). Apostain ELISA kit (Alexis Biochemicals, USA) uses the increased sensitivity of DNA in condensed chromatin of apoptotic cells to denaturation by formamide (Frankfurt and Krishan, 2001a), which is attributed, in part, to changes in the DNA-histone interactions. The increased sensitivity of cells with denatured DNA is detected by a monoclonal antibody specific for single-strand DNA (Mab F7-26) in an ELISA format (Frankfurt and Krishan, 2001b).

K562 cells were treated with the appropriate mycelium crude extracts and samples were collected 48 hours post-treatments. Apostain ELISA assay was performed according to manufacturer's instructions and as detailed in Materials and Methods.

K562 cells were plated in 6 well-plates at $1 \times 10^5$ cells/ml. Twenty-four hours later cells were treated with the mycelium crude extracts MH210, Meth178, MH17, Meth134, MC293, and MH428 at 250 µg/ml and 500 µg/ml (see Table 3). The tyrphostin AG957 at 10 µM and 20 µM was included as a positive control. In addition, a solvent-treated sample was included, in which DMSO was added to 0.6%. Forty-eight hours post treatment cells were counted and washed with cold PBS and subjected to Apostain ELISA Assay according to manufacturer's instruction. To calculate relative Apostain values, empty wells were subtracted from absorbance values obtained from cells treated with the different extracts. The solvent-treated sample was assigned the value 1, and relative values were calculated.

The data shown in Table 4 illustrate the ability of the various mycelium crude extracts to induce an increase in DNA condensation. Almost all crude extracts were able to induce a more than twofold increase in DNA condensation above the solvent-treated sample. Mycelium crude extracts Meth178, MH17, Meth134, MC293, and MH428 induced increases in DNA condensation to values of 4.3, 3.5 3.6, 5.3, and 2.8, respectively, after 48-hour treatments.

Furthermore, AG957, a known $p210^{Bcr-Abl}$ inhibitor (Kaur et al., 1994), also significantly induced an increase in DNA condensation at 10 µM. It is interesting that a higher dose of mycelium crude extracts caused a decrease in the measured signal, suggesting that at higher concentrations of mycelium extracts, cell death is mediated, in part, by necrosis.

TABLE 4

Apostain values from K562 cells treated with mycelium crude extracts

| Mycelium Extract | Relative Apostain Value | |
| --- | --- | --- |
| | 250 µg/ml | 500 µg/ml |
| MH210 | 1.9 | 1.9 |
| Meth178 | 4.3 | 1.4 |
| MH17 | 3.5 | 1.6 |
| Meth134 | 3.6 | 3.2 |
| MC293 | 5.3 | 6.5 |
| MH428 | 2.8 | 10.9 |
| AG957 | 6.2 | 3.9 |
| | (10 µM) | (20 µM) |

Example 5

Cleavage of PARP by the Mycelium Extracts

The execution of apoptosis requires specific molecular machinery, the central component of which is a family of proteases called caspases, which are cysteine proteases that cleave proteins after specific aspartate residues, in response to proapoptotic signals (Nicholson and Thomberry, 1997). During apoptosis, caspases activated in an amplifying proteolytic cascade, cleave one another in sequence (Raff, 1998). One of the most widely studied caspases, caspase 3, is classified as an effector caspase and cleaves death substrates such as the structural protein lamin and the nuclear protein PARP (McGowan et al., 1996).

K562 cells treated with the appropriate concentration of the mycelium crude extracts MH210, Meth178, MH17, Meth134, MC293, and MH428 for 48 hours and used to monitor cleavage of PARP as an indication of the activation of the apoptosis pathway. Presence of cleaved PARP was monitored by means of anti-PARP. Treatment with AG957, a known Bcr-Abl inhibitor (Kaur et al., 1994), significantly activates PARP cleavage, attesting that AG957 promotes apoptosis in K562 cells. Thus, K562 cells were plated in T25 flasks at $1 \times 10^5$ cells/ml. Twenty-four hours later, mycelium crude extracts MC293, MH428, tyrphostin AG957, MH210, Meth178, MH17, and Meth134 were added at 500 µg/ml and 250 µg/ml for 48 hours. Cell lysates were resolved into 8% SDS-polyacrylamide gel electrophoresis (SDS-PAGE) followed by transfer to nitrocellulose filters. Western blotting was performed (as described in Materials and Methods) in which monoclonal anti-PARP antibody was used (Santa Cruz Co., USA).

Figure 2A:
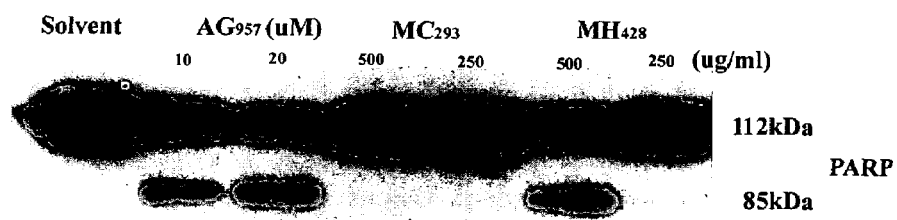
FIGS. 2A-2B depict Western blots showing cleavage of PARP by mushroom extracts. K562 cells were plated in T25 flasks at $1\times10^5$ cells/ml. Twenty-four hours later mycelium crude extracts MC293, MH428, tyrphostin AG957 (2A), MH210, Meth178, MH17, and Meth134 (2B) were added at 500 µg/ml and 250 µg/ml for 48 hours. Cell lysates were resolved into 8% SDS-polyacrylamide gel electrophoresis SDS-PAGE) followed by transfer to nitrocellulose filters. Western Blotting was performed as described in Materials and Methods in which monoclonal anti-PARP antibody was used (Santa Cruz, USA).
Figure 2B:
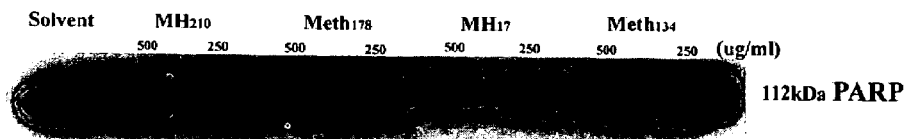

The results are shown in FIGS. 2A (MC293, MH428 and AG957) and 2B (MH210, Meth178, MH17, Meth134). Although most mycelium extracts shown failed to activate cleavage of PARP, extract MH428 significantly activated PARP cleavage.

Example 6

Mycelium Crude Extracts Induce Terminal Differentiation of K562 Cells

Leukemic blasts expressing p210 Bcr-Abl display arrested differentiation as well as resistance to apoptosis, even when exposed to high doses of anti-leukemic drugs (Bedi et al., 1995; Ray et al., 1996). K562 is a human erythroleukemia cell line derived from a patient with chronic myelogenous leukemia (Lozzio and Lozzio, 1975). These cells are pluripotent in that they are able to differentiate along a megakaryocytic, erythroid, or, to a lesser extent, monocytic lineage (Leary et al., 1987). Erythroid differentiation can be induced by a number of compounds, including hemin and butyric acid (Rowley et al., 1981). However, TPA (or PMA) treatment induces macrophage-like morphology and promotes the expression of proteins associated with megakaryocytes (Leary et al., 1987; Burger et al., 1992). Erythroid differentiation is frequently monitored by induced expression of hemoglobin, while megakaryocyte differentiation can be assessed by monitoring of the ability of treated K562 cells to reduce nitroblue tetrazolium (NBT) (Sutherland et al., 1986).

To assess erythroid differentiation, we monitored levels of hemoglobin production in treated cells using a commercially available kit (Sigma, USA). K562 cells were plated at $2 \times 10^5$ cell/ml in 6-well plates. Twenty-four hours later mycelium crude extracts at appropriate concentration were added. Growth of K562 cells in the presence of crude extracts was monitored by trypan blue exclusion assays (as described in Materials and Methods). Numbers of viable cells were monitored after 2 and 4 days post-treatment. On Day 5, cells were washed with PBS, cell pellet was lysed, and levels of hemoglobin were determined (as described in Materials and Methods). Hemoglobin levels were normalized to protein concentration in each sample. Relative hemoglobin levels were calculated in relation to solvent-treated sample, which was designated 1.0. The experiment was carried out in duplicate with minimal variations. This experiment was repeated twice with similar outcomes.

Levels of expressed hemoglobin assayed at day 5 post-treatment were normalized to the amount of total proteins present in each sample. Relative units of hemoglobin were calculated in relation to levels of hemoglobin found in solvent-treated samples (DMSO at 0.6%). The results summarized in Table 5 show that butyric acid was active in inducing hemoglobin expression in K562, which is in agreement with published data (Villeval et al., 1983). Furthermore, three mycelium crude extracts (Meth178, MH17 and MH428) were active in inducing hemoglobin expression above the levels of DMSO-treated cells. Extracts MH17 and MH428 induced hemoglobin expression 4.2 and 2.1 times higher, respectively, than the solvent-treated cells. It was interesting that extract Meth178 was the most potent extract (about 12 times higher than DMSO-treated cells) and was more active than butyric acid.

TABLE 5

Induction of hemoglobin expression in K562 cells by mycelium crude extracts

| Mushroom Species | Strain | Extract | Concentration (µg/ml) | Relative Hemoglobin |
|---|---|---|---|---|
| Kuehneromyces mutabilis | 114 | MH161 | 300 | 0.9 |
| Pleurotus eryngii | 202 | MH210 | 500 | 0.8 |
| Omphalotus olearius | 173 | Meth178 | 500 | 11.9 |
| Piptoporus betulinus | 241 | MH17 | 500 | 4.2 |
| Ganoderma adspersum | 349 | Meth134 | 500 | 0.7 |
| Panus conchatus | 396 | Meth114 | 300 | 0.2 |
| Hypsizygus ulmarium | 812 | MC293 | 300 | 0.8 |
| Trametes zonata | 540 | MH428 | 250 | 2.1 |
| Butyric Acid | | | 1 mM | 9.4 |

Example 7

Involvement of MAP Kinase p38 in Mediating Growth Inhibition of Mycelium Crude Extracts Previous reports indicated that proliferation and differentiation of K562 cells are mediated by mitogen-activated protein kinase (MAPK) pathway (Cobb, 1999; Cross et al., 2000). We examined the involvement of p38 MAPK in mediating the antiproliferative effect of the mycelium crude extracts. This was achieved by pretreatment of K562 cells with SB203580, a specific inhibitor of p38 kinase pathway, in the presence of the various mycelium crude extracts.

K562 cells were plated on 96 well-plates at $1.5 \times 10^4$ cells/well. Cells were pretreated with 10 µM of SB203580 (Calbiochem, USA) 24 hours later. Mycelium crude extracts (see Table 3) were added at 1 mg/ml hours 3 later and incubated for additional 24 hours. XTT assay was carried out as previously described. Growth inhibition was calculated as before and relative to solvent-treated samples. The experiment was performed in duplicate with minimal variations.

The data shown in Table 6 indicate that pretreatment of SB203580 resulted in a moderate relief of the growth inhibition caused by MH161, Meth178, and MH210 and no influence in MC293 and MH428 extracts. These results indicate that the antiproliferative function of Meth114, MH161, Meth178, MH17, and MH210 are partially dependent on p38. Furthermore, the p38 kinase pathway is not involved in mediating the antiproliferative effect of mycelium extracts MC293 and MH428.

TABLE 6

Involvement of MAP kinase p38 in the growth inhibition of K562 cells by mycelium extracts

| | | Inhibition of K562 | |
|---|---|---|---|
| Extract | Strain | — | SB203580 (10 µM) |
| Meth114 | 396 | 56 | 27.9 |
| MH161 | 114 | 61.3 | 34.3 |
| Meth178 | 173 | 56.9 | 40.2 |
| MH210 | 202 | 53.8 | 43.3 |
| MH17 | 241 | 68.8 | 46.3 |
| Meth134 | 349 | 59.2 | 47.6 |
| MC293 | 812 | 56.7 | 70.7 |
| MH428 | 540 | 69 | 80.3 |

Example 8

Effect of Mycelium Crude Extracts on the Expression of $p210^{Bcr-Abl}$ in K562 Cells Expression of $p210^{Bcr-Abl}$ hybrid protein is correlated with carcinogenesis in CML. A number of CML inhibitors have been found to exert their effect by down-regulating the expression of $p210^{Bcr-Abl}$. We examined the ability of our mycelium crude extracts to affect $p210^{Bcr-Abl}$ expression levels.

K562 cells were plated in T25 flasks at $1 \times 10^5$ cells/ml. Twenty-four hours later, tyrphostin AG957 (a small molecule inhibitor of the protein tyrosine kinase p145(abl) and its oncogenic derivative p210(bcr-abl)) and mushroom extracts MH210, Meth178, MH17 (3A), tyrphostin AG957, Meth134, MC293, and MH428 (3B) were added at 500 µg/ml and 250 µg/ml for 48 hours. Western blotting was performed (as described in Materials and Methods), in which monoclonal c-Abl antibody was used (Santa Cruz Co., USA). Filters were stripped and reprobed with loading control, monoclonal β-actin antibody (Santa Cruz Co., USA).

Figure 3A:
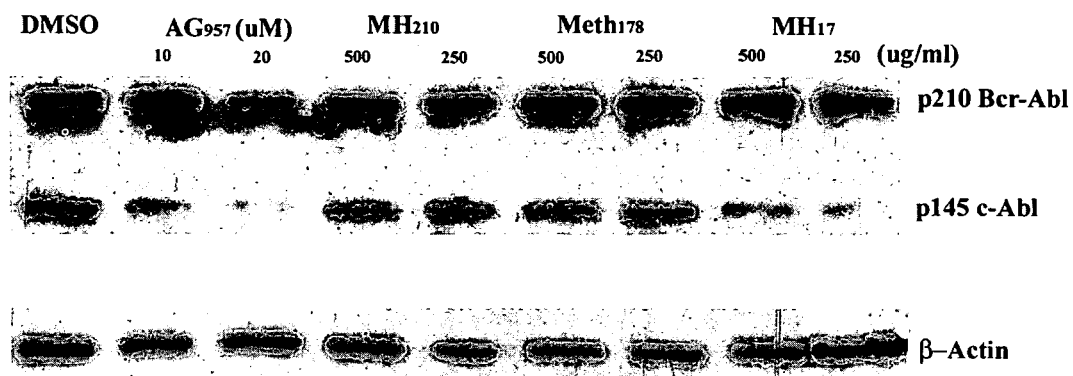
FIGS. 3A-3B depict Western blots showing the effect of mushroom extracts on the expression of $p210^{Bcr-Abl}$ in K562 cells. K562 cells were plated in T25 flasks at $1\times10^5$ cells/ml. Twenty-four hours later, tyrphostin AG957, mushroom extracts MH210, Meth178, MH17 (3A), tyrphostin AG957, Meth134, MC293, and MH428 (3B) were added at 500 µg/ml and 250 µg/ml for 48 hr. Western Blotting was performed as described in Materials and Methods, in which monoclonal c-Abl antibody was used (Santa Cruz, USA). Filters were stripped and re-probed with loading control, monoclonal β-actin antibody (Santa Cruz, USA).
Figure 3B:
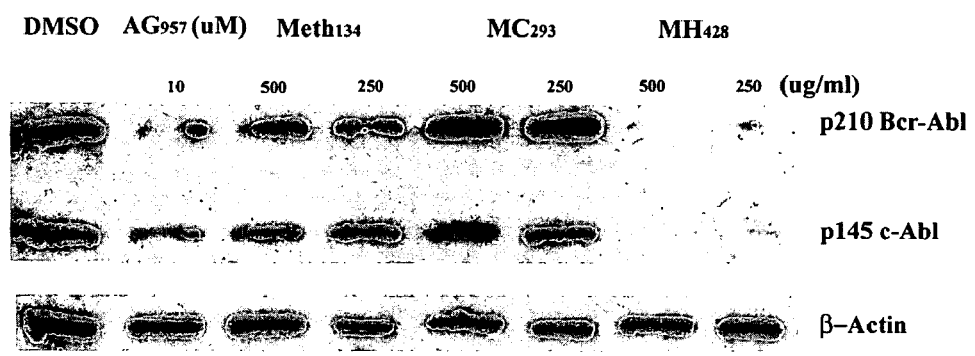

FIGS. 3A and 3B demonstrate that exposure of K562 cells to AG957 (10 µM and 20 µM), Meth134 (500 µg/ml and 250 µg/ml), MH428 (500 µg/ml and 250 µg/ml), and MH17 (500 µg/ml and 250 µg/ml) caused a reduction in Bcr-Abl protein levels in K562 cells with varying potency (Meth 134 shows a moderate reduction). In contrast, no significant effect on $p210^{Bcr-Abl}$ levels was observed with MH210, MC293, and Meth178 mycelium extracts. Interestingly, mycelium crude extract MH428 was the most potent of our selected crude extracts and caused a dramatic reduction in both $p210^{Bcr-Abl}$ and normal p145 c-Abl levels. Moreover, the reduction of $p210^{Bcr-Abl}$ and p145 c-Abl was specific, because no effect on levels of β-actin was detected.

Example 9

Identification of Mycelium Crude Extracts that Selectively Inhibit Proliferation of LNCaP Cells Mushroom crude extracts were tested for their ability to inhibit the growth of prostate cancer cells. We used the LNCaP cell line established from a metastatic lesion of human prostatic adenocarcinoma (Horoszewicz et al., 1983) as a representative of prostate cancer cell line—it is androgen-dependent for proliferation and expresses several markers of prostate cancer including the prostate-specific antigen (PSA).

LNCaP cells were plated in 96-well plates at $1.5 \times 10^4$ cells/well. Twenty-fours hours later, mycelium crude extracts were added for an additional 24 hours followed by XTT determination according to manufacturer's instructions (Biological Industries, Israel). Percentage of growth inhibition was calculated in relation to solvent-treated samples. Experiments were carried out in duplicate. The results are shown in Table 7. Changes in % coefficient of variance (CV) among duplicate samples were minimal.

TABLE 7

Effect of LNCaP-selective mycelium crude extracts on the growth of MH3924A, ABAE, HT-29 and cell lines

| | | | | % of Growth Inhibition | | | |
|---|---|---|---|---|---|---|---|
| Ext | Mushroom | Strain | Solvent | LNCaP | MH3924A | ABAE | HT-29 |
| Meth 162 | *Kuehneromyces mutabilis* | 114 | Eth | 60.4 | 26.0 | 25.1 | 18.9 |
| Meth 215 | *Pleurotus eryngii* | 202 | Eth | 64.2 | 19.5 | 41.7 | −1.5 |
| Meth 194 | *Pholiota aurivella* | 236 | Eth | 70.0 | −7.0 | −75.6 | 22.0 |
| Meth 134 | *Ganoderma adspersum* | 349 | Eth | 50.0 | −15.5 | −44.7 | 23.1 |
| Meth 114 | *Panus conchatus* | 396 | Eth | 52.4 | 11.5 | 27.8 | 4.3 |
| Meth 327 | *Trametes zonata* | 540 | Eth | 49.9 | 39.8 | 33.6 | 7.4 |

Mycelium crude extracts that inhibited LNCaP cell lines by 50% or more and also exhibited minimal growth inhibition against other cell lines were designated as selective LNCaP inhibitors. Table 7 shows a list of selective mycelium crude extracts (with their designations and identification of the mushroom strain in the first two columns) with percentage of growth inhibition applied to a variety of cell lines. Growth inhibition was calculated compared with solvent-treated samples.

Table 7 shows that a total of 6 mycelium crude extracts exhibited selective activity against LNCaP cell line with varying potency and selectivity. It is of interesting that all mycelium extracts active against LNCaP were prepared using 70% ethanol extraction.

Example 10

Resistance to Imatinib Mesylate (Gleevec) in CML Treatment

The tyrosine kinase p210 Bcr-Abl is the principal driving force in CML development, therefore modulators of its activity or function are expected to serve as CML therapeutics. Recently, imatinib mesylate (ST1571, Gleevec, Novartis, Basel, Switzerland) was introduced as a powerful inhibitor of the tyrosine kinase activity of p210 Bcr-Abl and, thereby, as an effective therapy for CML. Although imatinib mesylate produces high rates of complete clinical response in the chronic phase, resistance is universal and clinical relapse develops rapidly in the advanced phase of CML (Gorre et al., 2001). The majority of patients resistance to imatinib therapy coincides with reactivation of the tyrosine kinase activity of the Bcr-Abl fusion oncoprotein. This can result from gene amplification and, more importantly, from point mutations that disrupt the binding of imatinib to Bcr-Abl itself. More than 50%, and perhaps as many as 90%, of patients with CML relapse have Bcr-Abl point mutations in different amino acids scattered throughout the Abl kinase domain such as mutations of Thr-315 in the Abl kinase domain to Ile (T315I), the Tyr-253 to Phe (Y253F) or the E255K mutation.

The murine wild-type (WT) BaF3 pro-B-lymphocyte cell line depends on IL-3 for growth and viability, whereas the BaF3/p185, expressing the oncogenic p185 Bcr-Abl tyrosine kinase, became factor independent. The p185 Bcr-Abl (WT) as well as p185 Bcr-Abl carrying point mutations E255K or T315I were cloned into PSLXBcr-Abl vectors and used to transform BaF3 cells. Stable BaF3/p185bcr-abl clones were selected using appropriate antibiotics that were growing adherent on ECM proteins (van der Kulp et al., 2001). BaF3 cell lines were kindly provided by Dr. J. Duyster (Munich, Germany).

Figure 4:
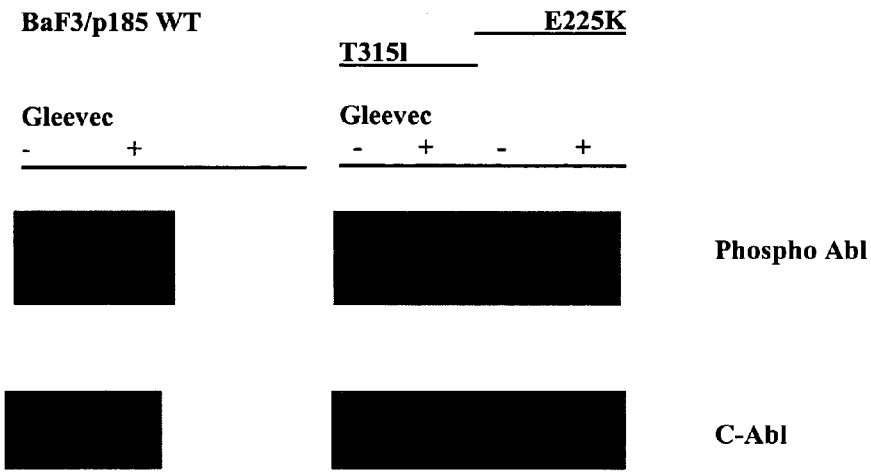
FIG. 4 depicts Western blots showing the effect of Gleevec on the phosphorylation of wild-type Bcr-Abl and mutated Bcr-Abl T315I and E255K.

BaF3 cell lines carrying WT Bcr-Abl were sensitive to treatment with Gleevec for both growth and phosphorylation of Bcr-Abl. However, BaF3 cells carrying mutated Bcr-Abl were resistant to Gleevec (Table 8 and FIG. 4). Table 8 shows that the $IC_{50}$ of Gleevec for BaF3 cell lines carrying WT Bcr-Abl was about 0.7 μM. However, the $IC_{50}$ using the mutant Bcr-Abl T315I was higher by about twenty fold (14 μM). In contrast, using extract of *Trametes zonata* mushroom in 100% dichloromethane (DCM540), the $IC_{50}$ with the two cell lines were comparable, indicating that the mushroom extract is effective in inhibiting the growth of both the wild-type and the mutation-carrying cell lines. FIG. 4 shows that treatment with 1 μM of Gleevec for 60 min causes significant reduction in phosphorylated WT Bcr-Abl, while no reduction in the level of phosphorylation was seen in mutated Bcr-Abl. In contrast, DCM540 was equally effective in inhibiting the phosphorylation of WT as well as mutated Bcr-Abl., indicating that the extract of *Trametes zonata* may be useful for treatment of CML and of Gleevec-refractory CML.

TABLE 8

Growth inhibition of BaF3/Bcr-Abl cell lines with organic extract of Trametes zonata

| Compound | $IC_{50}$ BaF3/p185 Bcr-Abl (WT) | BaF3/p185 Bcr-Abl T315I mutant |
|---|---|---|
| Trametes zonata | | |
| DCM organic extract (#540) | 211 µg/ml | 180 µg/ml |
| Gleevec (STI-571) | 0.7 µM | 14 µM |

Figure 5:
FIG. 5 depicts Western blots showing inhibition of Bcr-Abl phosphorylation in BaF3 cell lines by DCM540.
Figure 6:
FIG. 6 depicts Western blots showing inhibition of Bcr-Abl phosphorylation in K562 cell line by DCM540.
Figure 6:

K562, BaF3/Bcr-Abl WT, BaF3/Bcr-Abl T315I and BaF3/Bcr-Abl E255K cell lines were seeded 4 mls/well in 6-well plates 5-6×10$^5$ cells/ml. 24 hours post-plating, different concentrations of the appropriate extract or drug were added. Control cells were treated with 2% DMSO. Thus, cells were treated with 1 µM Gleevec and dichloromethane (DCM) extract of T. zonata # 540 at two concentrations: (A) at 500 µg/ml and (B) at 1000 µg/ml were added after 24 hours. Cells were treated for 60 min, then collected and centrifuged at 5000 rpm for 5 min. Cell pellets were lysed in lysis buffer {10 mM Tris, pH 7.4; 100 mM NaCl; 1 mM EDTA; 1 mM EGTA; 1 mM NaF; 20 mM $Na_4P_2O_7$; 2 mM $Na_3VO_4$; 1% Triton-X100; 10% glycerol; 0.1% SDS; 0.5% deoxycholate; 1 mM PMSF; 10 µl protease inhibitor cocktail and phosphatase inhibitor cocktail were added to every 1 ml lysate}. After that, 40 µg protein from each sample were separated on 8% SDS-PAGE, and Western blot was performed according to the manufacturer's instructions using phospho-c-Abl (Tyr245) Antibody (Cell Signaling Technology Co.) and c-Abl monoclonal antibody (Santa Cruz Biotechnology). FIG. 5 shows the inhibition of Bcr-Abl tyrosine kinase phosphorylation in BaF3 cells expressing the Bcr-Abl WT or the mutants Bcr-Abl T315I and Bcr-Abl E255K treated with the tyrosine kinase inhibitor Gleevec or the #540 extract at two different concentrations A and B. FIG. 6 shows the inhibition of Bcr-Abl tyrosine kinase phosphorylation in K562 cells treated with Gleevec (ST1571) or the #540 extract at the same two different concentrations as in FIG. 5.

Cell viability was determined using trypan blue exclusion assay. Number of cells obtained relative to untreated samples at 48 hours post-treatment were used to calculate percentage of inhibition and IC50 was calculated.

Discussion

CML is a malignancy of pluripotent hematopoietic cells characterized by the presence of the Philadelphia (Ph) chromosome, which results from reciprocal translocation between the long arms of chromosomes 9 and 22 {(t(9;22) q34;q11)} resulting in the creation of the fusion gene $p210^{Bcr-Abl}$. The bcr-abl fusion gene encodes a phosphoprotein (p210) that functions as a disregulated (abnormal) protein tyrosine kinase and predisposes the cell to become neoplastic. The presence of active $p210^{Bcr-Abl}$ renders CML cells resistant to apoptosis and delays differentiation.

Medicinal mushrooms have been an important source of therapeutic substances for the treatment of various human diseases. Antitumor activities from mushrooms were described by many reports (Mizuno, 1999; Wasser, 2002). In most cases, activity was due to high-molecular-weight polysaccharides with a molecular weight of 200-400,000 D. The antitumor activity of HMW polysaccharides was attributed to the immune-modulation function or enhancement properties of the immune system, and not to direct influence on the tumor cells. In the present invention, we attempted to identify mycelium crude extracts that directly show antitumor effects against cancer cells. Furthermore, we used various organic mixtures to prepare our mycelium crude extracts in an attempt to enrich them with low molecular weight moieties that can easily penetrate the cell wall.

Mycelium crude extracts prepared from our culture collection of Higher Basidiomycetes (these mushrooms are also available elsewhere) were evaluated for their ability to selectively inhibit the growth of the human CML 562 cell line. Using submerged conditions, we cultivated 42 species of Higher Basidiomycetes mushrooms and prepared 168 mycelium crude extracts by a variety of extraction methods (Table 1). Initially, we evaluated the ability of our mycelium crude extracts to inhibit the growth of K562 cells by more than 50% compared with the solvent-treated cells. Data shown in Table 2 illustrate that 44 extracts were active in inhibiting K562 cells. However, only 8 were found to exhibit a selective effect against K562 cells (Table 3). $IC_{50}$ values for the K562-selective extracts ranged from 250 to 500 µg/ml. Most of the selective extracts showed partial or complete cytostatic activity and only MH161 showed cytotoxic activity against K562 cells (FIG. 1).

The observed antiproliferative activity of the selective K562 mycelium crude extracts was attributed to induction of apoptosis by most extracts, as determined by Apostain ELISA assay. Our results indicate that growth inhibition was caused by the induction of the apoptosis pathway and not as a result of necrosis. However, higher concentration or longer exposure time can also cause death from necrosis, as indicated by a reduction in DNA condensation determined by the Apostain ELISA assay (Table 4). Data obtained by monitoring PARP cleavage as an indication of apoptosis illustrated that only our control AG957 and higher concentration of MH428, and not the other mycelium crude extracts could cause a significant cleavage of PARP. This might be explained by the fact that Apostain ELISA assay is a more sensitive measurement than the PARP cleavage assay. In addition, PARP cleavage assay measures a very late event in the apoptosis pathway, while Apostain measures a much earlier event. Thus, longer exposure times might be required to observe signs of apoptosis by the PARP cleavage assay.

Table 9 summarizes various characteristics of the extracts herein designated MH428, Meth178. MH17, MH210, MC293, Meth134, Meth114 and MH161.

TABLE 9

Characteristics of K562-selective mycelium crude extracts

| | MH 428 | Meth 178 | MH 17 | MH 210 | MC 293 | Meth 134 | Meth 114 | MH 161 |
|---|---|---|---|---|---|---|---|---|
| Selective Growth Inhibition of K562 cells | + | + | + | + | + | + | + | + |
| Down-regulation of Bcr-Abl | ++ | − | +/− | − | − | − | NT | NT |
| Induction of erythroid differentiation | + | +++ | ++ | − | − | − | − | − |
| PARP cleavage | + | − | − | + | − | − | NT | NT |
| Apostain | ++++ | + | + | + | +++ | ++ | NT | NT |
| Viability | Cytostatic | Cytostatic | Cytostatic | Cytostatic | Cytostatic | Cytostatic | Cytostatic | Cytostatic |

"+": positive activity;
"−": negative activity by.
NT: not tested.
"++" and "+++" "indicate greater potency of positive response.

K562 cells are pluripotent cells that are able to differentiate along a megakaryocytic, erythroid, or, to a lesser extent, monocytic lineage. Erythroid differentiation can be induced by a number of compounds including hemin and butyric acid (Villeval et al., 1983). K562 selective mycelium crude extracts were evaluated for their ability to induce erythroid differentiation in K562 cells. Three extracts, Meth178, MH17, and MH428, showed significant ability to induce hemoglobin production by a factor of 11.9, 4.2, and 2.1, respectively.

It is interesting that there was no correlation between the ability to induce apoptosis and to induce differentiation (Table 8). Mycelium crude extract Meth178 was the most potent in inducing erythroid differentiation. However, it was only a moderate inducer of apoptosis as determined by Apostain, and it failed to activate PARP cleavage. Conversely, MH428 extract showed weak activity in inducing erythroid differentiation, while it displayed the most significant apoptosis-inducing activity, as determined by both Apostain ELISA and PARP cleavage assays. Furthermore, mycelium extracts MC293 and Meth134 showed significant apoptosis activity as determined by Apostain ELISA assay, but failed to induce erythroid differentiation. Thus, the two activities are separable. At this stage, the molecular mechanism by which these mycelium extracts cause the induction of differentiation is not clear. It is worth noting that the hemoglobin produced in K562 is a fetal hemoglobin, mainly γ-globin. Increased expression of the endogenous γ-globin gene is a realistic approach to therapy of β-globin disorders such as sickle cell anemia and β-thalassemia (Nagel et al., 1985; Labie et al., 1985). Thus, our mycelium extracts, especially Meth178, has the potential to serve as a therapy for β-globin disorders.

The fusion protein $p210^{Bcr-Abl}$ plays a principal role in CML carcinogenesis. Consequently, down-regulation of $p210^{Bcr-Abl}$ is an appealing strategy for developing chemotherapeutics for the treatment of CML. We evaluated the ability of our mycelium crude extracts to lower expression levels of $p210^{Bcr-Abl}$. Our data revealed that MH428 significantly inhibited the expression of $p210^{Bcr-Abl}$, which was moderately inhibited by MH17. In contrast, the other extracts exerted a minor effect on the expression levels of $p210^{Bcr-Abl}$. The mechanism leading to down-regulation of $p210^{Bcr-Abl}$ by MH428 and MH17 is unclear. However, it is worth investigating whether this downregulation is caused by inhibition of the transcription of $p210^{Bcr-Abl}$ or by affecting protein degradation. A number of compounds such as geldanamycin and radicicol exhibited antiproliferative effect against K562 cells, mediated in part by downregulation of $p210^{Bcr-Abl}$ (Nimmanapalli et al., 2001; Shiotsu et al., 2000). Immune precipitation analysis showed that $p210^{Bcr-Abl}$ formed multiple complexes with heat shock protein 90 (Hsp90), some containing p23 and others Hsp70. The presence of geldanamycin (GA) decreased the association of $p210^{Bcr-Abl}$ with Hsp90 and p23 and increased its association with the chaperones Hsp70 and p60Hop. Loss of Hsp90/p23 association and acquisition of Hsp70/p60Hop preceded GA-induced degradation of $p210^{Bcr-Abl}$ (An et al., 2000).

The MAPK pathway includes the extra cellular signal-regulated kinase (ERK), the c-Jun N-terminal kinase (JNK), and the p38 kinase modules (Cross et al., 2000). Such signaling pathways regulate multiple biological activities, including cell proliferation, differentiation, and survivals (Cobb, 1999). The bulk of the evidence suggests that activation of the ERK pathway increases the cell death threshold (Ishikawa and Kitamura, 1999). Conversely, activation of the JNK and p38 kinase cascades is generally associated with enhanced activation of the apoptosis program (Ichijo et al., 1997). In an attempt to elucidate the mechanism of action of our mycelium crude extracts, we used potent and selective pharmacological inhibitors to investigate the role of p38 in mediating the antitumor effect of our mycelium crude extracts. Data shown in Table 6 argue that inhibition of MAPK p38 partially relieves growth inhibition caused by some mycelium crude extracts such as Meth178, MH17, Meth114, MH161, and MH210 but not by MC293 and MH428. This argues that MAPK p38 is not the principle mediator of the antiproliferative function of our K562-selective mycelium crude extracts. Similar analysis using additional pharmaceutical inhibitors targeting other second messenger pathways are required for the elucidation of the molecular pathways involved in mediating the anti-CML effect of our mycelium crude extracts.

REFERENCES

Allera C., Lazzarini G., Patrone E., Alberti I., Barboro P., Melchiori A., Parodi S., and Balbi C. 1997. The condensation of chromatin in apoptotic thymocytes shows a specific structural change. *J Biol Chem*, 272, 10817-10822.

An W. G., Schulte T. W., Neckers L. M. 2000. The heat shock protein 90 antagonist geldanamycin alters chaperone association with p210bcr-abl and v-src proteins before their degradation by the proteasome. *Cell Growth Differ*, 11, 355-60.

Bedi A., Barber J. P., Bedi G. C., el-Deiry W. S., Sidransky D., Vala M. S., Akhtar A. J., Hilton J., and Jones R. J. 1995. BCR-ABL-mediated inhibition of apoptosis with delay of G2/M transition after DNA damage: a mechanism of resistance to multiple anticancer agents. *Blood*, 86, 1148-1158.

Burger S. R., Zutter M. M., Sturgill-Koszycki S., and Santoro S. A. 1992. Induced cell surface expression of functional alpha-2/beta-1 integrin during megakaryocytic differentiation of K562 leukemic cells. *Exp Cell Res*, 202, 28-35.

Chang S. T. 2001. A 40-year journey through bioconversion of lignocellulosic wastes to mushrooms and dietary supplements. *Int J Med Mush*, 3, 299-310.

Clarkson B. D., Strife A., Wisniewski D., Lambek C., and Carpino N. 1997. New understanding of the pathogenesis of CML: A prototype of early neoplasia. *Leukemia*, 11, 1404-1428.

Cobb M. H. 1999. MAP kinase pathways. *Prog Biophys Mol Biol*, 71, 479-500.

Cortez D., Reuther G., and Pendergast A. M., 1997. The Bcr-Abl tyrosine kinase activates mitogenic signaling pathways and stimulates G1-to-S phase transition in hematopoietic cells. *Oncogene*, 15, 2333-2342.

Cross T. G., Scheel-Toellner D., Henriquez N. V., Deacon E., Salmon M., and Lord J. M. 2000. Serine/threonine protein kinases and apoptosis. *Exp Cell Res*, 256, 34-41.

Dou Q. P., McGuire T. F., Peng Y., and An B. 1999. Proteasome inhibition leads to significant reduction of Bcr-Abl expression and subsequent induction of apoptosis in K562 human chronic myelogenous leukemia cells. *J Pharm Exp Ther*, 289, 781-790.

Drexler H G, MacLeod R A, Uphoff C C. 1999. Leukemia cell lines: in vitro models for the study of Philadelphia chromosome-positive leukemia. *Leuk Res*. 23(3):207-15.

Frankfurt O., and Krishan A. 2001a. Identification of apoptotic cells by formamide-induced DNA denaturation in condensed chromatin: *Histochem Cytochem*, 49, 369-378.

Frankfurt O., and Krishan A. 2001b. Enzyme-linked immunosorbent assay (ELISA) for the specific detection of apoptotic cells and its application to rapid drug screening. *J Immunol Methods*, 253, 133-144.

Freshney R. I. 1987. Culture of Animal Cells. In: *A Manual of Basic Technique*, Wiley-Liss., ed. New York, 245-256.

Gorre M E, Mohammed M, Ellwood K, Hsu N, paquette R, Rao P N, Sawyers C L. 2001. Clinical resistance to STI-571 cancer therapy caused by BCR-ABL gene mutation or amplification. *Science*. 293: 876-880.

Hawksworth D. L. 2001. Mushrooms: The extent of the unexplored potential. *Int J Med Mush*, 3, 333-337.

Horoszewicz J S, Leong S S, Kawinski E, Karr J P, Rosenthal H, Chu T M, Mirand E A, Murphy G P. 1983. LNCaP model of human prostatic carcinoma. *Cancer Res*. 43(4), 1809-1818.

Hsieh T. C., and Wu J. M. 2001. Cell growth and gene modulatory activities of Yunzhi (Windsor Wunxi) from mushroom *Trametes versicolor* in androgen-dependent and androgen-insensitive human prostate cancer cells. *Int J Oncol*, 18, 81-88.

Ichijo H., Nishida E., Irie K., ten Dijke P., Saitoh M., Moriguchi T., Takagi M., Matsumoto K., Miyazono K., and Gotoh Y. 1997. Induction of apoptosis by ASK1, a mammalian MAPKKK that activates SAPK/JNK and p38 signaling pathways. *Science* (Washington D.C.), 275, 90-94.

Ikekawa T. 2001. Beneficial effect of edible and medicinal mushrooms on health care. *Int J Med Mush*, 3, 290-298.

Ishikawa Y. and Kitamura M. 1999. Dual potential of extracellular signal-regulated kinase for the control of cell survival. *Biochem Biophys Res Commun*, 264, 696-701.

Kaur G., Gazit A., Levitzki A., Stowe E., Cooney D. A., and Sausville E. A. 1994. Tyrphostin induced growth inhibition: correlation with effect on p210bcr-abl autokinase activity in K562 chronic myelogenous leukemia. *Anticancer Drugs*, 5, 213-222.

Kirk P. M., Cannon P. F., David J. C., and Stalpers J. A. 2001. *Ainsworth and Bisby's dictionary of fungi*. 9th edn-.CAB International, Wallingford, 655 pp.

Labie D., Pagnier J., Lapoumeroulie C., Rouabhi F., Dunda-Belkhodja O., Chardin P., Beldjord C., Wajcman H., Fabry M. E. and Nagel R. L. 1985. Common haplotype dependency of high G gamma-globin gene expression and high Hb F levels in beta-thalassemia and sickle cell anemia patients. *Proc Natl Acad Sci USA*, 82, 2111-2114.

Leary J. F., Ohlsson-Wilhelm B. M., Giuliano R., LaBella S., Farley B., and Rowley P. T. 1987. Multipotent human hematopoietic cell line K562: Lineage-specific constitutive and inducible antigens. *Leuk Res*, 11, 807-815.

Lozzio C. B., and Lozzio B. B. 1975. Properties and usefulness of the original K-562 human myelogenous leukemia cell line. *Blood*, 45, 321-334.

McGahon A. J., Bissonnette R., Schmitt M., Cotter K. M., Green D. R., and Cotter T. G. 1994. BCR-ABL maintains resistance of chronic myelogenous leukemia cells to apoptotic cell death. *Blood*, 83, 1179-1187.

McGowan A. J., Ruiz-Ruiz M. C., Gorman A. M., Lopez-Rivas A., and Cotter T. G. 1996. Reactive oxygen intermediate(s) (ROI): Common mediator(s) of poly(ADP-ribose) polymerase (PARP) cleavage and apoptosis. *FEBS Lett*, 392, 299-303.

Mizuno T. 1999. The extraction and development of antitumor-active polysaccharides from medicinal mushrooms in Japan (review). *Int J Med Mush*, 1, 9-29.

Mosmann T. 1983. Rapid colorimetric assay for cellular growth and survival: application to proliferation and cytotoxicity assays. *J Immunol Methods*, 65, 55-63.

Nagel R. L., Fabry M. E., Pagnier J., Zohoun I., Wajcman H., Baudin V. and Labie D. 1985. Hematologically and genetically distinct forms of sickle cell anemia in Africa. The Senegal type and the Benin type. *N Engl J Med*, 312, 880-884.

Nicholson D. W., and Thomberry N. A. 1997. Caspases: Killer proteases. *Trends Biol Sci*, 22, 299-306.

Nimmanapalli R., O'Bryan E., Bhalla K. 2001. Geldanamycin and its analogue 17-allylamino-17-demethoxygeldanamycin lower Bcr-Abl levels and induces apoptosis and differentiation of Bcr-Abl-positive human leukemic blasts. *Cancer Res*, 61, 1799-804.

Raff M. 1998. Cell suicide for beginners. *Nature* (Lond), 396, 119-122.

Ray S., Bullock G., Nuñez G., Tang C., Ibrado A. M., Huang Y., and Bhalla K. 1996. Enforced expression of Bcl-xS induces differentiation and sensitizes CML-blast crisis K562 cells to Ara-C mediated differentiation and apoptosis. *Cell Growth Differ*, 7, 1617-1623.

Roehm N. W., Rodgers G. H., Hatfield S. M., and Glasebrook A. L. 1991. An improved colorimetric assay for cell proliferation and viability utilizing the tetrazolium salt XTT. *J Immunol Methods*, 142, 257-265.

Rowley P. T., Ohlsson-Wilhelm B. M., Farley B. A., and Labella S. 1981. Inducers of erythroid differentiation in K562 human leukemia cells. *Exp Hematol*, 9, 32-37.

Shiotsu Y, Neckers L M, Wortman I, An W G, Schulte T W, Soga S, Murakata C, Tamaoki T, Akinaga S. 2000. Novel oxime derivatives of radicicol induce erythroid differentiation associated with preferential G(1) phase accumulation against chronic myelogenous leukemia cells through destabilization of Bcr-Abl with Hsp90 complex. *Blood*, 96, 2284-2291.

Sutherland, J. A., Turner, A. R., Mannoni, P., McGann, L. E., Turc, J. M. 1986. Differentiation of K562 leukemia cells along erythroid, macrophage, and megakaryocyte lineages. *J Biol Response Mod*, 5, 250-256.

Tomatis A., Melnick R. L., Haseman J., Barrett J. C., Huff J. 2001. Alleged 'misconceptions' distort perceptions of environmental cancer risks. *FASEB Journal*, 15, 195-203.

Urbano A., Koc Y., and Foss F. M. 1998. Arginine butyrate down-regulates p210 bcr-abl expression and induces apoptosis in chronic myelogenous leukemia cells. *Leukemia*, 12, 930-936.

van der Kuip H, Goetz A W, Miething C, Duyster J, Aulitzky W E. 2001. Adhesion to fibronectin selectively protects Bcr-Abl+ cells from DNA damage-induced apoptosis. *Blood*, 98, 1532-1541.

Villeval J. L., Pelicci P. G., Tabilio A., Titeux M., Henri A., Houesche F., Thomopoulos P., Vainchenker W., Garbaz M., Rochant H., Breton-Gorius J., Edwards P. A., Testa U. 1983. Erythroid properties of K562 cells. Effect of hemin, butyrate and TPA induction. *Exp Cell Res*, 146, 428-35.

Wasser S. P. 2002. Medicinal mushrooms as a source of antitumor and immunomodulating polysaccharides. *Appl Microbiol Biotechnol*, 60, 258-274.

Wasser S. P., Nevo E., Sokolov D., Reshetnikov S., Timor-Tismenetsky M. 2000. Dietary supplement from medicinal mushrooms: diversity of types and variety of regulations. *Int J Med Mush*, 2, 1-19.

Wasser S. P., Lewinsohn D., Duckman I. 2002. *Culture collection of higher Basidiomycetes of the Haifa University*, Peledfus, Haifa, 76 pp.

What is claimed is:

1. A method for treatment of Philadelphia Chromosome-positive Leukemia, comprising
administering to a patient in need thereof a therapeutically effective amount of a mycelium extract from *Trametes zonata*, wherein said mycelium extract is obtained by extraction of a dry mycelium of said mushroom with an extraction solvent comprising one or more organic solvents selected from the group consisting of methanol, ethanol, acetonitrile, ethyl acetate, chloroform, hexane, cyclohexane, isooctane, and dichloromethane.

2. The method according to claim 1 wherein said extraction solvent is a non-aqueous organic solvent.

3. The method according to claim 2 wherein said organic solvent is selected from the group consisting of methanol, ethanol, dichloromethane and ethyl acetate.

4. The method according to claim 1 wherein said extraction solvent is an aqueous organic solvent.

5. The method according to claim 4 wherein said extraction solvent is 70% ethanol or a mixture of ethyl acetate and methanol.

6. The method according to claim 1 wherein said Philadelphia Chromosome-positive Leukemia is chronic myelogenous leukemia (CML) or Ph+ acute lymphoblastic leukemia (ALL).

7. The method according to claim 1 wherein said mycelium extract is further concentrated and purified to obtain a concentrated and purified mycelium extract.

8. The method of claim 7 wherein the concentrated mycelium extract is purified by column chromatography (TLC), fractional distillation, preparative thin layer chromatography (TLC), preparative high performance liquid chromatography (HPLC), or centrifugal partition chromatography (CPC).

* * * * *